US012667660B2

(12) United States Patent
 Yang

(10) Patent No.: US 12,667,660 B2
(45) Date of Patent: *Jun. 30, 2026

(54) BILATERALLY DRIVEN CLOSED-LOOP ARTIFICIAL PANCREAS

(71) Applicant: MEDTRUM TECHNOLOGIES INC., Shanghai (CN)

(72) Inventor: Cuijun Yang, Shanghai (CN)

(73) Assignee: MEDTRUM TECHNOLOGIES INC., Shanghai (CN)

( * ) Notice: Subject to any disclaimer, the term of this patent is extended or adjusted under 35 U.S.C. 154(b) by 865 days.

This patent is subject to a terminal disclaimer.

(21) Appl. No.: 17/923,915

(22) PCT Filed: Aug. 26, 2020

(86) PCT No.: PCT/CN2020/111181
 § 371 (c)(1),
 (2) Date: Nov. 8, 2022

(87) PCT Pub. No.: WO2021/227298
 PCT Pub. Date: Nov. 18, 2021

(65) Prior Publication Data
 US 2023/0173165 A1     Jun. 8, 2023

(30) Foreign Application Priority Data

May 14, 2020     (WO) ................ PCT/CN2020/090152

(51) Int. Cl.
 A61M 5/145          (2006.01)
 A61M 5/14           (2006.01)
 (Continued)

(52) U.S. Cl.
 CPC ............ A61M 5/1452 (2013.01); A61M 5/14 (2013.01); A61M 5/14236 (2013.01);
 (Continued)

(58) Field of Classification Search
 CPC ...... A61M 5/1454; A61M 2005/14506; A61M 5/1452; A61M 5/14; A61M 5/14236;
 (Continued)

(56) References Cited

U.S. PATENT DOCUMENTS

| | | | | | |
|---|---|---|---|---|---|
| 2003/0199824 | A1* | 10/2003 | Mahoney | ............ | A61M 5/1452 |
| | | | | | 604/155 |
| 2003/0236498 | A1* | 12/2003 | Gross | ................ | A61M 5/14216 |
| | | | | | 604/141 |
| 2019/0117881 | A1 | 4/2019 | Yang | | |

FOREIGN PATENT DOCUMENTS

| CN | 101208515 | 6/2008 |
|---|---|---|
| CN | 108261585 | 7/2018 |

(Continued)

OTHER PUBLICATIONS

"International Search Report (Form PCT/ISA/210) of PCT/CN2020/111181," mailed on Feb. 22, 2021, pp. 1-2.

*Primary Examiner* — Chelsea E Stinson
*Assistant Examiner* — Eric A Lange
(74) *Attorney, Agent, or Firm* — JCIP GLOBAL INC.

(57)          ABSTRACT

A bilaterally driven closed-loop artificial pancreas, includes: a detection module; an infusion module, the infusion module includes: a drug storage unit; a screw and a driving wheel provided with wheel teeth, the driving wheel driving the screw and the screw pushing a piston; a driving unit cooperating with the driving wheel, the driving unit including at least two driving portions; a power unit connected to the driving unit, the power unit outputting two forces in two directions on the driving unit; and a program module. The power unit is controlled by the program module. The artificial pancreas has higher infusion efficiency and can enhance user experience.

7 Claims, 4 Drawing Sheets

(51) Int. Cl.

| | | |
|---|---|---|
| *A61M 5/142* | (2006.01) | |
| *A61M 5/168* | (2006.01) | |
| *A61M 5/172* | (2006.01) | |
| *G16H 20/17* | (2018.01) | |

(52) U.S. Cl.
CPC .... *A61M 5/14248* (2013.01); *A61M 5/16804* (2013.01); *A61M 5/172* (2013.01); *G16H 20/17* (2018.01); *A61M 2005/14208* (2013.01); *A61M 2005/14506* (2013.01); *A61M 2205/3327* (2013.01); *A61M 2205/36* (2013.01); *A61M 2230/201* (2013.01)

(58) Field of Classification Search
CPC .......... A61M 5/14248; A61M 5/16804; A61M 5/172; A61M 2005/14208; A61M 5/20; A61M 5/31; G16H 20/17
See application file for complete search history.

(56) References Cited

FOREIGN PATENT DOCUMENTS

| | | | | | |
|---|---|---|---|---|---|
| CN | 108261585 A | * | 7/2018 | .......... | A61M 5/1723 |
| CN | 108472440 | | 8/2018 | | |
| WO | WO-2006104806 A2 | * | 10/2006 | ........ | A61M 5/14546 |

* cited by examiner

BILATERALLY DRIVEN CLOSED-LOOP ARTIFICIAL PANCREAS

CROSS-REFERENCE TO RELATED APPLICATION

This application is a 371 of international application of PCT application serial no. PCT/CN2020/111181, filed on Aug. 26, 2020, which claims the priority benefit of China application no. PCT/CN2020/090152, filed on May 14, 2020. The entirety of each of the above-mentioned patent applications is hereby incorporated by reference herein and made a part of this specification.

TECHNICAL FIELD

The present invention mainly relates to the field of medical instruments, in particular to a bilaterally driven closed-loop artificial pancreas.

BACKGROUND

The pancreas in a normal person can automatically monitor the amount of glucose in the blood and automatically secrete the required dosage of insulin/glucagon. However, for diabetic patients, the function of the pancreas is abnormal, and the pancreas cannot normally secrete required dosage of insulin. Therefore, diabetes is a metabolic disease caused by abnormal pancreatic function and also a lifelong disease. At present, medical technology cannot cure diabetes, but can only control the onset and development of diabetes and its complications by stabilizing blood glucose.

Patients with diabetes need to check their blood glucose before injecting insulin into the body. At present, most of the detection methods can continuously detect blood glucose, and send the blood glucose data to the remote device in real time for the user to view. This detection method is called Continuous Glucose Monitoring (CGM), which requires the detection device to be attached to the surface of the patients' skin, and the sensor carried by the device is inserted into the subcutaneous tissue fluid for testing. According to the blood glucose (BG) level, the infusion device, as a closed-loop or semi-closed-loop artificial pancreas, injects the currently required insulin dose. At present, the detection device and the infusion device are connected to each other to form a closed-loop artificial pancreas with the processing of the program module.

However, the driving method of the closed-loop artificial pancreas in prior art is relatively simple, which worsens user experience, making the infusion efficiency low.

Therefore, there is an urgent need for a closed-loop artificial pancreas with diverse driving methods and higher infusion efficiency.

BRIEF SUMMARY OF THE INVENTION

Embodiments of the present invention disclose a bilaterally driven closed-loop artificial pancreas with diverse driving method for infusion and higher infusion efficiency, enhancing user experience.

The invention discloses a bilaterally driven closed-loop artificial pancreas, comprising: a detection module configured to detect blood glucose; an infusion module, including: a drug storage unit; a screw connected to a piston and a driving wheel provided with wheel teeth, respectively, the driving wheel drives the screw to move by rotation, pushing the piston, provided in the drug storage unit, forward; a driving unit cooperating with the driving wheel, the driving unit includes at least two driving portions, the driving unit pivots around a pivot shaft, driving different driving portions in different directions, thus pushing the wheel teeth located on different driving wheel respectively, and rotating the driving wheel; a power unit, connected to the driving unit, outputs two forces in two directions on the driving unit, making the driving unit pivot in two directions around the pivot shaft; and a program module connected to the detention module and the infusion module respectively, the force output by the power unit is controlled by the program module, thereby controlling the infusion module to infuse insulin required.

According to one aspect of this invention, the driving wheel includes at least two sub-wheels.

According to one aspect of this invention, the driving wheel includes two sub-wheels, and the pivot shaft is disposed between the two sub-wheels, one or more of the driving portions are provided on both sides of the driving unit, and each sub-wheel is cooperated with each driving portion.

According to one aspect of this invention, two driving portions are respectively provided on both sides of the driving unit, and the two driving portions on one side of the driving unit are disposed up and down or left and right.

According to one aspect of the present invention, the power unit includes an electric-heated linear actuator or an electric-driven linear actuator.

According to one aspect of the present invention, the driving unit has a variety of different pivot amplitudes or pivot rates, making the infusion module have a variety of different infusion increments or infusion rates.

According to one aspect of the present invention, any two of the detection module, the program module and the infusion module are connected to each other configured to form a single structure whose attached position on the shin is different from the third module.

According to one aspect of the present invention, the detection module, the program module and the infusion module are connected together configured to form a single structure which is attached on only one position on the skin.

Compared with the prior arts, the technical solution of the present invention has the following advantages:

In the bilaterally driven closed-loop artificial pancreas disclosed herein, a power unit connected to the driving unit, the power unit outputs two forces in two directions on the driving unit, making the driving unit pivot in two directions around the pivot shaft. The driving unit can drive the driving wheel in two directions for infusion insulin, improving the infusion efficiency. Additionally, with the driving unit pivoting in two directions, the infusion module has multiple infusion modes.

Furthermore, the driving unit has a variety of different pivot amplitudes or pivot rates, making the infusion module have a variety of different infusion increments or infusion rates. Controlled by the program module, the driving unit can pivot with different amplitudes; also, the driving unit has multiple pivot rates, changing the infusion rates of the infusion module. And according to body condition, user can chose suitable or different infusion modes, optimizing the infusion process and accurately controlling the blood glucose level.

Furthermore, the detection module, the program module and the infusion module are connected together configured to form a single structure which is attached on only one position on the skin. If the three modules are connected as a whole and attached in the only one position, the number of the device on the user skin will be reduced, thereby reducing the interference of more attached devices on user activities. At the same time, it also effectively solves the problem of the poor wireless communication between separating devices, further enhancing the user experience.

BRIEF DESCRIPTION OF THE DRAWINGS

FIG. 3b is a side view of the driving unit in FIG. 3a;

DETAILED DESCRIPTION

Figure 1:
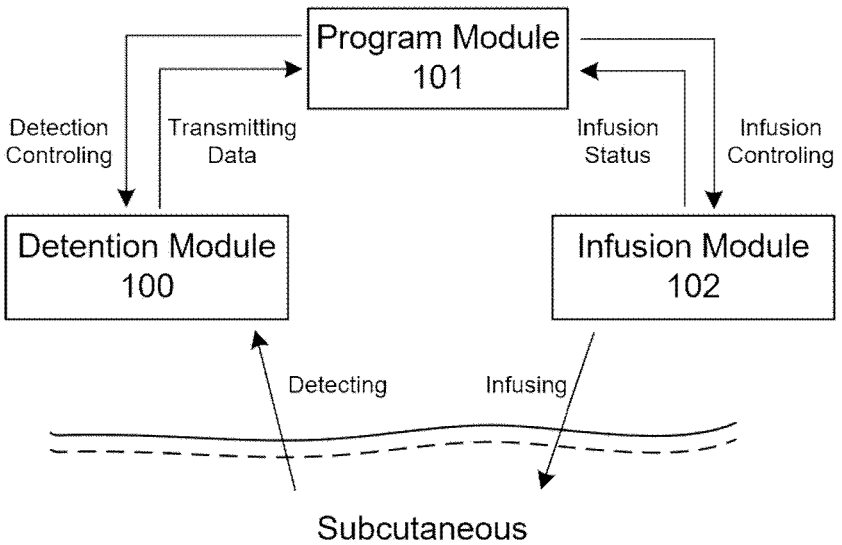
FIG. 1 is a schematic view of the module relationship of the closed-loop artificial pancreas according to one embodiment of the present invention.

As described above, in the prior art device, the driving method of the closed-loop artificial pancreas in prior art is relatively simple, which worsens user experience, making the infusion efficiency low.

The study found that the cause of the above problems is that the driving unit can only drive the driving wheel in one rotation direction.

In order to solve this problem, the present invention provides a bilaterally driven closed-loop artificial pancreas, in which the driving unit can drive the driving wheel in two directions for infusion insulin, making the infusion module have multiple infusion modes, enhancing user experience.

Various exemplary embodiments of the present invention will now be described in detail with reference to the drawings. The relative arrangement of the components and the steps, numerical expressions and numerical values set forth in the embodiments are not to be construed as limiting the scope of the invention.

In addition, it should be understood that, for ease of description, the dimensions of the various components shown in the figures are not necessarily drawn in the actual scale relationship, for example, the thickness, width, length or distance of certain units may be exaggerated relative to other structures.

The following description of the exemplary embodiments is merely illustrative, and is not intended to be in any way limiting the invention and its application or use. The techniques, methods and devices that are known to those of ordinary skill in the art may not be discussed in detail, but such techniques, methods and devices should be considered as part of the specification.

It should be noted that similar reference numerals and letters indicate similar items in the following figures. Therefore, once an item is defined or illustrated in a drawing, it will not be discussed further in the following description of the drawings.

FIG. 1 is a schematic view of the module relationship of the closed-loop artificial pancreas according to the embodiment of the present invention.

The closed-loop artificial pancreas disclosed in the embodiment of the present invention mainly includes a detection module 100, a program module 101, and an infusion module 102.

The detection module 100 is used to continuously detect the user's real-time blood glucose (BG) level.

Generally, the detection module 100 is a Continuous Glucose Monitoring (CGM) for detecting real-time BG, monitoring BG changes, and also sending them to the program module 101.

The program module 101 is used to control the detection module 100 and the infusion module 102. Therefore, the program module 101 is connected to the detection module 100 and the infusion module 102, respectively. Here, the connection refers to a conventional electrical connection or a wireless connection.

The infusion module 102 includes the essential mechanical structures used to infuse insulin and controlled by the program module 101, which will be described in detail below. According to the current insulin infusion dose calculated by the program module 101, the infusion module 102 injects the currently insulin dose required into the user's body. At the same time, the real-time infusion status of the infusion module 102 can also be fed back to the program module 101.

The embodiment of the present invention does not limit the specific positions and connection relationships of the detection module 100, the program module 101 and the infusion module 102, as long as the aforementioned functional conditions can be satisfied.

As in an embodiment of the present invention, the three are electrically connected to form a single structure. Therefore, the three modules can be attached together on only one position of the user's skin. If the three modules are connected as a whole and attached in the only one position, the number of the device on the user skin will be reduced, thereby reducing the interference of more attached devices on user activities. At the same time, it also effectively solves the problem of the poor wireless communication between separating devices, further enhancing the user experience.

As in another embodiment of the present invention, the program module 101 and the infusion module 102 are electrically connected to each other to form a single structure while the detection module 100 is separately provided in another structure. At this time, the detection module 100 and the program module 101 transmit wireless signals to each other to realize mutual connection. Therefore, the program module 101 and the infusion module 102 can be attached on the same position of the user's skin while the detection module 100 is attached on the other position.

As in another embodiment of the present invention, the program module 101 and the detection module 100 are electrically connected to each other forming a single structure while the infusion module 102 is separately provided in another structure. The infusion module 102 and the program module 101 transmit wireless signals to each other to realize mutual connection. Therefore, the program module 101 and the detection module 100 can be attached on the same position of the user's skin while the infusion module 102 is attached on the other position.

As in another embodiment of the present invention, the three are respectively provided in different structures, thus being attached on different position. At this time, the program module 101, the detection module 100 and the infusion module 102 respectively transmit wireless signals to each other to realize mutual connection.

It should be noted that the program module 101 of the embodiment of the present invention also has functions such as storage, recording, and access to the database, thus, the program module 101 can be reused. In this way, not only can the user's physical condition data be stored, but also the production cost and the user's consumption cost can be saved. As described above, when the service life of the detection module 100 or the infusion module 102 expires, the program module 101 can be separated from the detection module 100, the infusion module 102, or both the detection module 100 and the infusion module 102.

Generally, the service lives of the detection module 100, the program module 101 and the infusion module 102 are different. Therefore, when the three are electrically connected to each other to form a single device, the three can also be separated from each other in pairs. For example, if one module expires firstly, the user can only replace this module and keep the other two modules continuous using.

Here, it should be noted that the program module 101 of the embodiment of the present invention may also include multiple sub-modules. According to the functions of the sub-modules, different sub-modules can be respectively assembled in different structure, which is not specific limitation herein, as long as the control conditions of the program module 101 can be satisfied.

Figure 2A:
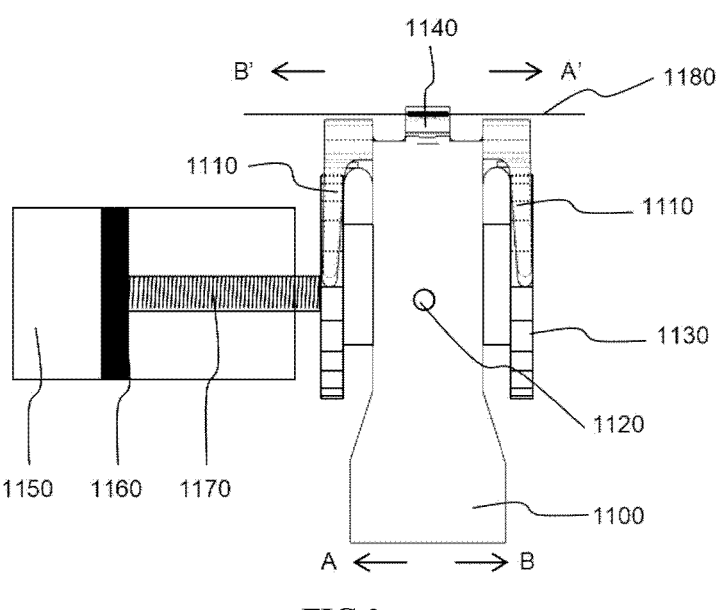
FIG. 2a-FIG. 2b are schematic views showing the structure of the infusion module according to an embodiment of the present invention.
Figure 2B:
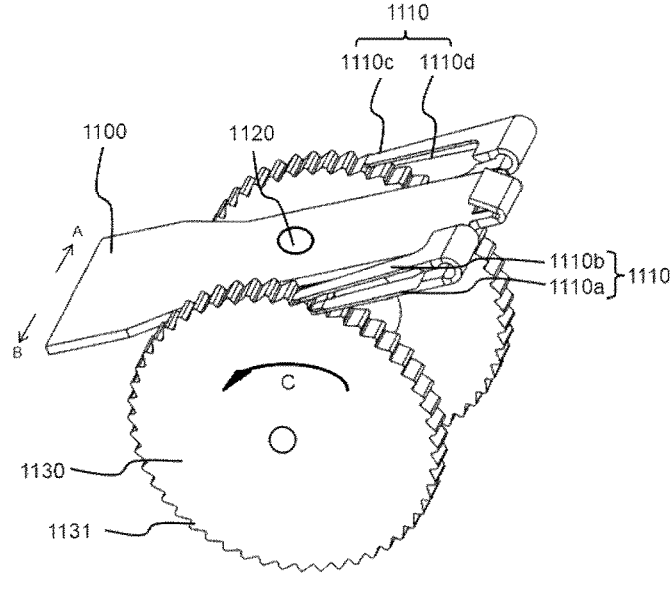

FIG. 2a is a schematic view showing the structure of the infusion module according to an embodiment of the present invention. FIG. 2b is a schematic view of the cooperation between the driving unit 1100 and the driving wheel 1130 according to an embodiment of the present invention.

The infusion module includes a driving unit 1100, a driving wheel 1130, a drug storage unit 1150, a piston 1160, a screw 1170, and a power unit 1180.

The screw 1170 is connected to the piston 1160 and the driving wheel 1130, respectively. In the embodiment of the present invention, the driving wheel 1130 is movably mounted on the device base (not shown), and the driving wheel 1130 moves the driving screw 1170 through rotation to advance the piston 1160 disposed in the drug storage unit 1150 to move forward for the purpose of injecting insulin.

The driving unit 1100 is used to drive the driving wheel 1130 to rotate. The driving unit 1100 is movably connected to the device base through the pivot shaft 1120. The power unit 1180 is used to apply a force to the driving unit 1100 leading the driving unit 1100 to pivot. In the embodiment of the present invention, the power unit 1180 is fixedly connected at the top position 1140 of the driving unit 1100, thereby dividing the power unit 1180 into two left and right portions, such as the A' direction portion and the B' direction portion in FIG. 2a. The driving unit 1100 is alternately led to pivot in the A' direction or the B' direction through the pivot shaft 1120. Preferably, in the embodiment of the present invention, when the power unit 1180 leads the driving unit 1100 to A' direction, the driving unit 1100 pivots in the A direction through the pivot shaft 1120, while the power unit 1180 leads the driving unit 1100 to the B' direction, the driving unit 1100 pivots in the B direction through the pivot shaft 1120. By alternately leading the driving unit 1100 to the A' direction and the B' direction, the driving unit 1100 can be alternately pivoted through the pivot shaft 1120 in two different directions, like the A direction and the B direction.

The power unit includes an electric-heated linear actuator or an electric-driven linear actuator. Preferably, in the embodiment of the present invention, the power unit 1180 is made of shape memory alloy. The A' direction portion and the B' direction portion of the shape memory alloy are alternately powered on and off, and a leading force is applied to the driving unit 1100 by a change in the length of the power unit 1180 thereof. The power unit 1180 may be composed of one piece of shape memory alloy, or may be composed of left and right segments (such as the A' direction segment and the B' direction segment) of shape memory alloy, and is not specifically limited herein, as long as the force can be applied to lead the driving unit 1100 to pivot.

Here, it should be noted that the power unit 1180 includes, but is not limited to, a shape memory alloy. In other embodiments of the present invention, the power unit 1180 may also be other structures, and the location where the power unit 1180 applies force to the driving unit 1100 is also not limited to the top position 1140, as long as the action of applying a force to the driving unit 1100 can be satisfied to cause the driving unit 1100 to alternately pivot left and right.

As shown in FIG. 2a and FIG. 2b, the driving wheel 1130 includes a plurality of sub-wheels, and the circumferential surface of the sub-wheels is provided with wheel teeth 1131. Driving unit 1100, through the wheel teeth 1131, cooperates with the driving wheel 1130.

In the embodiment of the present invention, a plurality of driving portions 1110 are installed on each side of the driving unit 1100. Therefore, a plurality of sub-wheels are also installed on both sides of the driving unit 1100 to cooperate with the driving portions 1110. Preferably, in the embodiment of the present invention, the driving unit 1100 includes four driving portions 1110, which are 1110a, 1110b, 1110c, and 1110d, respectively. 1110a, 1110b are installed on one side of the driving unit 1100, while 1110c, 1110d are installed on the other side of the driving unit 1100. The driving wheel 1130 includes two sub-wheels, one of which cooperates with 1110a, 1110b and the other of which cooperates with 1110c, 1110d.

Figure 3A:
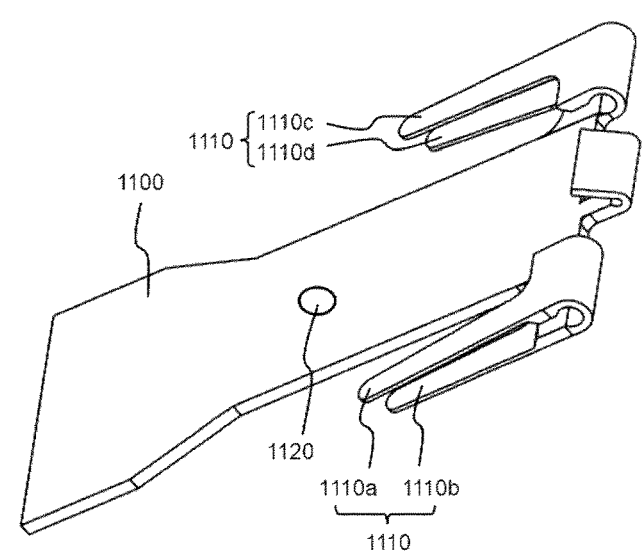
FIG. 3a is a schematic view of the driving unit according to an embodiment of the present invention.
Figure 3B:
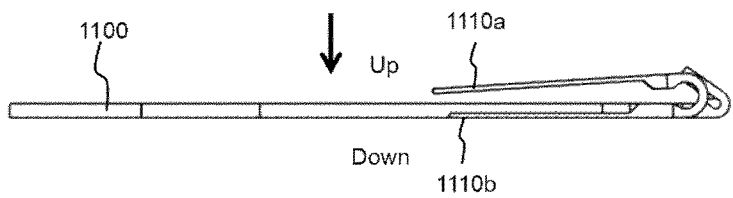

FIG. 3a and FIG. 3b are respectively schematic view, a side view of the driving unit 1100.

In the embodiment of the present invention, the two driving portions 1110 on one side of the driving unit 1100 are installed up and down. Here, the up and down settings refer to the up and down positional relationship representations shown in FIG. 3b. Preferably, the two driving portions 1110 (such as 1110a and 1110b) on the side of the driving unit 1100 can be seen in the side view FIGS. 3b, and 1110b and 1110d are blocked by 1110a and 1110c, respectively.

It should be noted that, in other embodiments of the present invention, these four driving portions may be disposed by other means, such as the two driving portions on one side of the driving unit are disposed left and right, as long as the arms are able to drive the driving wheel to rotate, and is not specifically limited herein.

Figure 4:
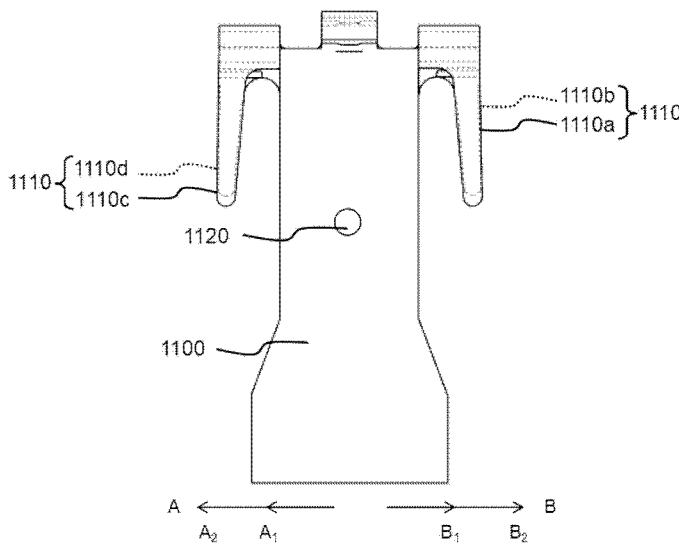
FIG. 4 is a schematic view of a position structure of multiple pivot amplitudes of the driving unit according to an embodiment of the present invention.

FIG. 4 is a schematic view of a position structure of a plurality of pivot amplitudes of the driving unit 1100, and is also a top view in the direction of the arrow in FIG. 3b.

In a single pivot in the direction A, driving portion 1110a and/or 1110b engage the wheel teeth 1131 to rotate the driving wheel 1130, while 1110c and 1110d can slide on the wheel teeth 1131, but not exert a force for driving the driving wheel 1130 to rotate. And obviously, 1110c slides to the next adjacent driving position firstly. At this time, the driving unit 1100 stops pivoting and the driving portions 1110a and/or 1110b stop engaging the wheel teeth 1131, therefore, the driving wheel 1130 stops rotating. Thus, the driving unit 1100 completes one kind of pivot amplitude. At this time, the driving unit 1100 pivots in the A direction to reach $A_1$ position. The next moment the driving unit 1100 continues to pivot in the A direction, 1110d will slide to the next adjacent driving position. Similarly, the driving unit 1100 completes another kind of pivot amplitude. At this time, the driving unit 1100 still pivots in the A direction to reach $A_2$ position. And the driving unit 1100 completes the whole process of single pivot in the A direction, performing $A_1$ and $A_2$ two pivot amplitudes, respectively, thereby driving the driving wheel 1130 to rotate by two steps, realizing two kinds of infusion modes of the infusion module.

It should be noted that, in the above pivoting process, the driving portion 1110*d* may firstly slide to the next gear tooth 1131, and then 1110*c* slides to the next gear tooth 1131, which is not specifically limited herein. Similarly, when the driving unit 1100 pivots in the B direction, it can perform $B_1$ and $B_2$ two pivot amplitudes, respectively.

Obviously, in the whole process of the above-mentioned single pivot in the A direction, the driving unit 1100 undergoes an alternate action of pivot and stop, and the driving portions 1110 alternately engage and stop engaging wheel teeth 1131 to drive the driving wheel 1130 to rotate and stop rotating, realizing two-step rotation of the driving wheel, and finally achieving two infusion modes of the infusion module.

Referring to FIG. 4 again, in another embodiment of the present invention, the driving unit 1100 pivots to the $A_1$ position, and then pivots one or two amplitudes in the B direction, that is, reaching the $B_1$ or $B_2$ position until the pivot in the B direction stops. This process completes the alternate pivot of the driving unit 1100 in two directions, so that the driving wheel 1130 can be rotated in multiple steps. Therefore, in the embodiment of the present invention, the driving unit 1100 can alternately switch amplitudes among $A_1$-$B_1$, or $A_1$-$B_1$-$B_2$, or $B_1$-$A_1$-$A_2$, so as to achieve the purpose of switching among different infusion modes.

Referring to FIG. 4 again, in another embodiment of the present invention, the driving unit 1100 can also be pivoted directly to the $A_2$ position without passing through the $A_1$ position, then directly pivoted to the $B_2$ position without passing through the $B_1$ position, that is, the driving unit 1100 alternately pivots between the $A_2$-$B_2$ positions. As described above, the driving unit 1100 can also alternately pivot between the $A_1$-$B_1$ positions.

As with the infusion module of the embodiment of the present invention, when the infusion is started, the amount of insulin required is relatively large, and the patient or the artificial pancreas can select the large $A_2$-$B_2$ pivot amplitude for infusion. After a period of time, the intermediate $A_1$-$B_1$-$B_2$ pivot amplitude or $B_1$-$A_1$-$A_2$ pivot amplitude can be used to reduce the rate of insulin infusion. When the insulin infusion is about to be completed, the patient or the artificial pancreas can switch to the small $A_1$-$B_1$ pivot amplitude to further reduce the infusion rate and achieve precise control of the insulin infusion. Of course, the patient or the artificial pancreas can also choose one or several of the modes for infusion, and there are no specific restrictions.

It should be noted that in another embodiment of the present invention, further more driving portions, like three, four, etc., can be disposed on one side of the driving unit. And the total number of driving portions may also be an odd number, such as three, five or more, that is, the numbers of driving portions on both sides of the driving unit are not equal. Moreover, the structural relationship between the different driving portions can be similar to that described above, and no specific restrictions are imposed herein.

Figure 5A:
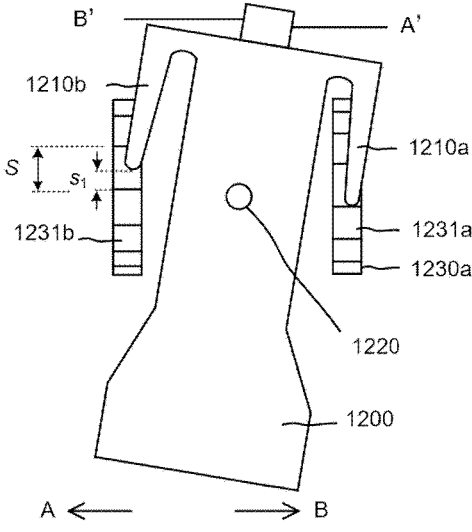
FIG. 5a-FIG. 5b are schematic views of the driving unit including two driving portions according to another embodiment of the present invention.
Figure 5B:
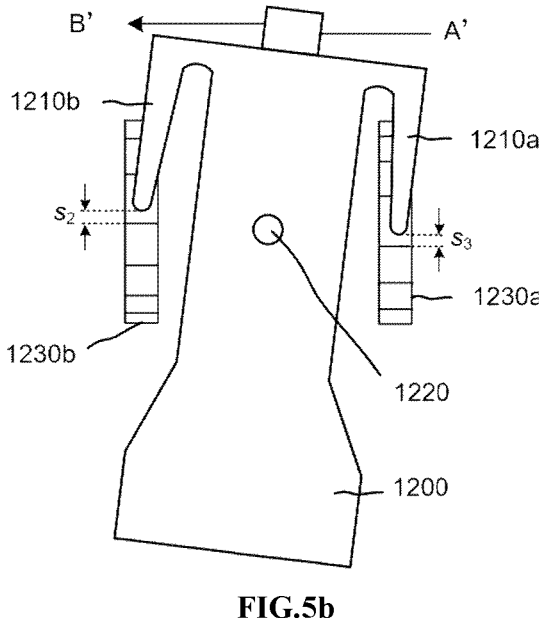

FIG. 5*a*-FIG. 5*b* are schematic views of the driving unit 1200 including two driving portions.

As described above, when the driving unit 1200 is output a force in the A' direction, the driving unit 1200 rotates in the A direction around the pivot shaft 1220, making the driving portion 1210*a* push the wheel teeth 1231*a*, thereby driving the driving wheel 1230*a* to rotate. When the driving unit 1200 is output a force in the B' direction, the driving unit 1200 rotates in the B direction around the pivot shaft 1220, making the driving portion 1210*b* push the wheel teeth 1231*b*, thereby driving the driving wheel 1230*b* to rotate.

Referring to FIG. 5*a* and FIG. 5*b* again, when the driving portion 1210*a* or 1210*b* reaches a different position, the driving unit 1200 can still continue to rotate in the direction A or B to move the driving portion away from the driving position. If the distance of the driving portion 1210*a* away from the driving position is $s_1$, if the tooth pitch is S, then $s_1$=1/3S, 1/2S, 3/4S, or S. Therefore, during the pivot of the driving unit 1200, at a certain moment, neither of the driving portions 1210*a* and 1210*b* push the wheel teeth 1231, for example, the front end of the driving portion and the driving position are separated by $s_2$ and $s_3$, respectively. At this time, the driving wheel does not rotate, nor does the infusion module perform insulin infusion. According to this working principle, the driving unit 1200 will pivot at any different amplitude, and the infusion module has a variety of different infusion modes.

In the embodiments of the present invention, the frequency of the force output by the power unit can be changed to further change the pivot frequency of the driving unit, so that the infusion module has a variety of different infusion rates. The user or the artificial pancreas can flexibly select the appropriate infusion rate as needed, making the infusion process flexible and controllable.

In summary, the present invention discloses a bilaterally driven closed-loop artificial pancreas with higher infusion efficiency and diverse infusion modes, enhancing user experience.

While the invention has been described in detail with reference to the specific embodiments of the present invention, it should be understood that it will be appreciated by those skilled in the art that the above embodiments may be modified without departing from the scope and spirit of the invention. The scope of the invention is defined by the appended claims.

The invention claimed is:

1. A bilaterally driven closed-loop artificial pancreas, comprising:
   a detection module configured to continuously detect a real-time blood glucose level;
   an infusion module, including:
   a drug storage unit;
   a screw connected to a piston and a driving wheel provided with wheel teeth, the driving wheel drives the screw to move by rotation, pushing the piston, provided in the drug storage unit, forward;
   a driving unit cooperating with the driving wheel, the driving unit includes at least two driving portions, the driving unit pivots around a pivot shaft, driving the driving portions in different directions, thus pushing the wheel teeth located on the driving wheel respectively, and rotating the driving wheel;
   a power unit connected to the driving unit, outputting two forces in two directions on the driving unit, making the driving unit pivot in two directions around the pivot shaft; and
   a program module, connected to the detection module and the infusion module, the forces output by the power unit are controlled by the program module, thereby controlling the infusion module to infuse insulin required, wherein the driving unit has a variety of different pivot amplitudes, making the infusion module have a variety of different infusion increments or infusion rates.

2. The bilaterally driven closed-loop artificial pancreas of claim 1, wherein the driving wheel includes at least two sub-wheels.

3. The bilaterally driven closed-loop artificial pancreas of claim 1, wherein the driving wheel includes two sub-wheels, and the pivot shaft is disposed between the two sub-wheels, at least one of the driving portions is provided on each of both sides of the driving unit, and each of the sub-wheels is cooperated with a corresponding one of the driving portions.

4. The bilaterally driven closed-loop artificial pancreas of claim 3, wherein the at least one driving portion on each of both sides of the driving unit is two driving portions, and the two driving portions on one of the sides of the driving unit are disposed up and down or left and right with respect to each other and the driving wheel.

5. The bilaterally driven closed-loop artificial pancreas of claim 1, wherein the power unit includes an electric-heated linear actuator or an electric-driven linear actuator.

6. The bilaterally driven closed-loop artificial pancreas of claim 1, wherein two of the detection module, the program module and the infusion module are connected to each other configured to form a single structure whose attached position on a skin is different from an attached position of a rest one of the detection module, the program module and the infusion module on the skin.

7. The bilaterally driven closed-loop artificial pancreas of claim 1, wherein the detection module, the program module and the infusion module are connected together configured to form a single structure which is attached on only one position on a skin.

\* \* \* \* \*